(12) United States Patent
Janik et al.

(10) Patent No.: US 7,253,901 B2
(45) Date of Patent: Aug. 7, 2007

(54) LASER-BASED CLEANING DEVICE FOR FILM ANALYSIS TOOL

(75) Inventors: Gary R. Janik, Palo Alto, CA (US); Patrick M. Maxton, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 857 days.

(21) Appl. No.: 10/056,271

(22) Filed: Jan. 23, 2002

(65) Prior Publication Data

US 2003/0137662 A1 Jul. 24, 2003

(51) Int. Cl.
| | |
|---|---|
| G01J 4/00 | (2006.01) |
| G01N 21/55 | (2006.01) |
| G01N 23/00 | (2006.01) |
| G01N 21/86 | (2006.01) |
| G01N 23/223 | (2006.01) |
| G01B 11/30 | (2006.01) |
| G01B 11/24 | (2006.01) |
| G01B 11/28 | (2006.01) |
| G01B 15/02 | (2006.01) |
| G02F 1/01 | (2006.01) |
| H01J 40/14 | (2006.01) |
| G21K 7/00 | (2006.01) |
| G01V 8/00 | (2006.01) |
| G01R 31/26 | (2006.01) |
| G01R 27/26 | (2006.01) |
| G01R 31/305 | (2006.01) |
| G01R 31/302 | (2006.01) |
| H01L 21/66 | (2006.01) |
| G01T 1/36 | (2006.01) |
| B08B 3/12 | (2006.01) |
| B08B 6/00 | (2006.01) |
| B08B 7/00 | (2006.01) |
| B08B 7/02 | (2006.01) |
| C25F 1/00 | (2006.01) |
| C25F 3/30 | (2006.01) |
| C25F 5/00 | (2006.01) |

(52) U.S. Cl. ............... 356/369; 356/445; 356/600; 356/601; 356/630; 250/225; 250/310; 250/559.27; 438/16; 438/17; 324/658; 324/719; 324/751; 324/752; 378/44; 378/70; 378/89; 134/1; 134/1.3

(58) Field of Classification Search ............ 438/7, 438/10, 16, 17; 134/1, 1.2, 1.1, 1.3; 204/157.15, 204/157.4, 157.41, 157.44; 356/364, 369, 356/337–343, 600, 601, 612, 445–448; 250/225; 324/751, 752, 719, 658
See application file for complete search history.

(56) References Cited

U.S. PATENT DOCUMENTS 4,588,885 A * 5/1986 Lovoi et al. ............... 134/1

(Continued)

Primary Examiner—Layla G. Lauchman
Assistant Examiner—Gordon J. Stock, Jr.
(74) Attorney, Agent, or Firm—Bever, Hoffman & Harms, LLP; Jeanette S. Harms

(57) ABSTRACT

A system for analyzing a thin film uses an energy beam, such as a laser beam, to remove a portion of a contaminant layer formed on the thin film surface. This cleaning operation removes only enough of the contaminant layer to allow analysis of the underlying thin film, thereby enhancing analysis throughput while minimizing the chances of recontamination and/or damage to the thin film. An energy beam source can be readily incorporated into a conventional thin film analysis tool, thereby minimizing total analysis system footprint. Throughput can be maximized by focusing the probe beam (or probe structure) for the analysis operation at the same location as the energy beam so that repositioning is not required after the cleaning operation. Alternatively, the probe beam (structure) and the energy beam can be directed at different locations to reduce the chances of contamination of the analysis optics.

28 Claims, 3 Drawing Sheets

U.S. PATENT DOCUMENTS

| | | | | |
|---|---|---|---|---|
| 4,876,983 A * | 10/1989 | Fukuda et al. | | 118/722 |
| 4,975,141 A | 12/1990 | Greco et al. | | |
| 5,204,517 A * | 4/1993 | Cates et al. | | 134/1 |
| 5,281,798 A * | 1/1994 | Hamm et al. | | 250/205 |
| 5,336,636 A * | 8/1994 | Burmer | | 438/675 |
| 5,465,154 A * | 11/1995 | Levy | | 356/632 |
| 5,485,091 A | 1/1996 | Verkuil | | |
| 5,608,526 A | 3/1997 | Piwonka-Corle et al. | | |
| 5,643,472 A | 7/1997 | Engelsberg et al. | | |
| 5,666,063 A * | 9/1997 | Abercrombie et al. | | 324/754 |
| 5,669,979 A * | 9/1997 | Elliott et al. | | 134/1 |
| 5,747,813 A | 5/1998 | Norton et al. | | |
| 5,814,165 A * | 9/1998 | Tatah et al. | | 148/565 |
| 6,261,853 B1 | 7/2001 | Howell et al. | | |
| 6,274,393 B1 * | 8/2001 | Hartswick | | 438/14 |
| 6,325,078 B2 | 12/2001 | Kamieniecki | | |
| 6,333,485 B1 * | 12/2001 | Haight et al. | | 219/121.68 |
| 6,355,494 B1 * | 3/2002 | Livengood et al. | | 438/14 |
| 6,383,824 B1 * | 5/2002 | Lensing | | 438/14 |
| 6,472,295 B1 * | 10/2002 | Morris et al. | | 438/463 |
| 6,621,281 B1 * | 9/2003 | Birdsley et al. | | 324/751 |
| 6,771,374 B1 * | 8/2004 | Rangarajan et al. | | 356/445 |
| 6,930,771 B2 * | 8/2005 | Rosencwaig et al. | | 356/237.1 |
| 7,006,222 B2 * | 2/2006 | Krishnan | | 356/369 |
| 7,110,113 B1 * | 9/2006 | Janik et al. | | 356/369 |

OTHER PUBLICATIONS

Pending U.S. Appl. No. 10/005,610 entitled "Method and Apparatus For Improved X-Ray Reflection Measurement"; Janik et al., filed Nov. 7, 2001.

* cited by examiner

LASER-BASED CLEANING DEVICE FOR FILM ANALYSIS TOOL

BACKGROUND OF THE INVENTION

1. Field of the Invention

The present invention relates to field of thin film measurement, and in particular to a method and apparatus for cleaning the surface of a thin film to improve measurement accuracy.

2. Background of the Invention

As the dimensions of semiconductor devices continue to shrink, accurate and efficient characterization of the components forming those devices becomes more critical. Typically, the manufacturing process for modern semiconductor devices includes the formation of a number of layers or "thin films" on a silicon wafer. The thin films can include oxide, nitride, and/or metal layers, among others. To ensure proper performance of the finished semiconductor devices, the thickness and composition of each thin film formed during the manufacturing process must be tightly controlled.

Modern thin films have reached the point where the accuracy and reproducibility of thin film measurements can be limited by contamination on the surface of the thin film. For example, the absorption of water and other vapors onto the thin film can create a contaminant layer that adversely affects thin film analysis techniques such as optical ellipsometry, optical reflectometry, grazing-incidence x-ray reflectometry (GXR), x-ray fluorescence (XRF), electron microprobe analysis (EMP), and non-contact electrical analysis—all of which operate by directing a probe beam (optical, x-ray, electron or corona discharge) at the surface of the thin film to be measured. The contaminant layer can also interfere with measurements techniques that physically contact the surface of the thin film, such as contact-based electrical analysis (e.g., spreading resistance analysis).

Conventional methods for cleaning thin films heat the entire wafer in an oven to a temperature of about 300° C. to vaporize any contaminant layer. FIG. 1a shows a conventional oven-based wafer cleaning system 100a used to prepare a wafer 110 for thin film analysis, as described in U.S. Pat. No. 6,325,078, issued Dec. 4, 2001 to Kamieniecki. Wafer 110 includes a thin film layer 112 formed on a silicon substrate 111, and a contaminant layer 113 formed on the surface of thin film layer 112. Wafer cleaning system 100a comprises a wafer stage 120 and multiple heat lamps 130. Wafer stage 120 positions wafer 110 under heat lamps 130, where thermal radiation from heat lamps 130 heats wafer 110 to vaporize contaminant layer 113. It is believed that this cleaning process is aided by the optical photons from heat lamps 130 effectively breaking bonds between contaminant layer 113 and thin film layer 112.

FIG. 1b shows another conventional wafer cleaning system 100b used to prepare wafer 110 for thin film analysis, as described in U.S. Pat. No. 6,261,853, issued Jul. 17, 2001 to Howell et al. Just as described with respect to FIG. 1a, wafer 110 includes a thin film layer 112 formed on a silicon substrate 111 and a contaminant layer 113 formed on the surface of thin film layer 112. Cleaning system 100b incorporates a stage 140 that includes a heating element 141. Heat generated by heating element 141 is conducted through stage 140 into wafer 110, thereby providing the heating required to vaporize contaminant layer 113. A heat exchanger 150 coupled to stage 140 captures excess heat from heating element 141, thereby minimizing undesirable heating of cleaning system 100b itself and the surrounding environment.

Although wafer cleaning systems 100a and 100b use different thermal energy sources (i.e., heat lamps 130 and heating element 141, respectively), both systems perform a bulk heating operation to remove contaminant layer 113. The large thermal control components (e.g., lamps, heated stages, heat exchangers, etc.) typically used for bulk wafer heating undesirably increase the cleanroom space required for these conventional cleaning systems. Further exacerbating the problem of excess equipment size, conventional cleaning systems are sometimes stand-alone units used in conjunction with a thin film analysis tool. Therefore, conventional cleaning systems can significantly increase the total footprint required for a complete thin film analysis system. The use of a separate cleaning system also has an adverse effect on throughput, as time must be spent transferring the wafer to and from the cleaning system. In addition, contaminants can redeposit on the cleaned wafer when it is transferred from the cleaning system to the film analysis tool.

In an attempt to somewhat alleviate these equipment size and recontamination problems, attempts have been made to combine wafer cleaning and measurement capabilities in a single tool. For example, the aforementioned U.S. Pat. No. 6,261,853 describes integrating cleaning system 100b with an existing metrology tool (Opti-Probe 5240 from Therma-Wave, Inc.). Also, the Quantox XP tool from KLA-Tencor integrates a wafer cleaning system similar to cleaning system 100b with a non-contact electrical film measurement system. However, any bulk wafer heating system must still incorporate the aforementioned (large) thermal control components. Furthermore, even if a combined system is used, the bulk heating operation can significantly degrade overall wafer processing throughput. Several seconds are required to heat the wafer to the temperature required for removal of the contaminant layer, and another several seconds are required to cool down the wafer after cleaning. Any wafer handling operations that must be performed during and after the cleaning operation (e.g., transferring the wafer from the cleaning system to the thin film analysis system) further reduce the throughput.

Accordingly, it is desirable to provide an efficient wafer cleaning system for thin film measurement systems that does not require lengthy heating and cooling times and does not require dedicated wafer handling steps.

SUMMARY

The present invention provides localized contaminant layer removal from a thin film surface, thereby enabling accurate and repeatable analysis of the thin film by a measurement tool. By using a concentrated energy beam to clean only the portion of the thin film to be measured by the measurement tool, the thin film analysis can be performed without the long heating and cooling times associated with conventional cleaning systems. Furthermore, the compact components used in an energy beam-based cleaning system can be incorporated into the thin film measurement tool itself, thereby eliminating any delays related to transferring the wafer to and from a stand-alone cleaning system. This integration also minimizes the total footprint required for a thin film analysis system, and since the wafer can be cleaned and analyzed in the same process chamber, redeposition of contaminants on the cleaned portion of the wafer can be prevented.

A thin film analysis system in accordance with an embodiment of the present invention comprises an energy beam source, an analysis module, and a stage. The stage holds a test sample (such as a wafer) that includes a thin film layer to be measured by the analysis module. The analysis module can comprise any thin film analysis system or systems, including a single-wavelength ellipsometer (SWE, such as described in co-owned, co-pending U.S. patent application Ser. No. 09/298,007), a spectroscopic ellipsometer (SE, such as described in co-owned U.S. Pat. No. 5,608,526), a reflectometer (such as described in co-owned U.S. Pat. No. 5,747,813), a non-contact electrical measurement system (such as described in co-owned U.S. Pat. No. 5,485,091), a GXR system (such as described in co-owned, co-pending U.S. patent application [Attorney Docket KLA-001]), a contact-based electrical measurement system, an XRF system, and/or an EMP system. More generally, this cleaning system can be used with any sort of inspection or metrology system used in the production of semiconductor devices. According to an embodiment of the present invention, the energy beam source is incorporated into a conventional thin film analysis tool, thereby minimizing the total footprint of the thin film analysis system.

The energy beam source is configured to direct an energy beam at a contaminant layer on the surface of the thin film layer. The energy beam heats a portion of the contaminant layer until that portion of the contaminant layer is vaporized. This process can be aided by direct photon excitation of the bonds between the contaminant layer and the thin film layer. The area of the thin film layer exposed by this cleaning operation can then be analyzed by the analysis module. The size of this analysis area required by the analysis module for performance of the thin film analysis can be used to determine the minimum required power and size of the energy beam. By minimizing the power and size of the energy beam, the risk of damage to the test sample is small. This risk of damage can be further reduced by performing the cleaning and measuring operations at non-functional regions of the test sample. According to an embodiment of the present invention, the energy beam source can comprise a laser, such as a Q-switched pulsed laser. According to another embodiment of the present invention, the energy beam source can comprise a flashlamp with appropriate focusing optics.

According to an embodiment of the present invention, a probe beam generated by the analysis module (e.g., a low-power laser beam, a white light beam, a corona discharge, an x-ray beam, etc.) is directed at the same location on the test sample as the energy beam produced by the energy beam source. Alternatively, a physical probe structure (e.g., a four-point probe in a spreading resistance tool) (can be aimed at the same location on the test sample as the energy beam produced by the energy beam source. Consequently, the test sample does not need to be moved between the cleaning and measurement operations, thereby maximizing analysis throughput. Furthermore, because the measurement operation can be performed immediately after the cleaning operation, the chances of the cleaned portion of the thin film layer (i.e., the analysis area) being recontaminated before the measurement operation are minimized.

According to another embodiment of the present invention, the probe beam (or probe structure) from the analysis module and the energy beam are directed at different locations on the test sample. The test sample (and/or the analysis module) is then repositioned after the cleaning operation to align the probe beam (or probe structure) with the analysis area of the thin film layer. This allows the focusing optics or probe structure of the analysis module to be kept out of the vicinity of the portion of the contaminant layer being vaporized, thereby minimizing the risk of any contaminant redeposition on the measurement focusing optics or probe structure.

The present invention will be more fully understood in view of the following description and drawings.

DETAILED DESCRIPTION

Figure 1A:
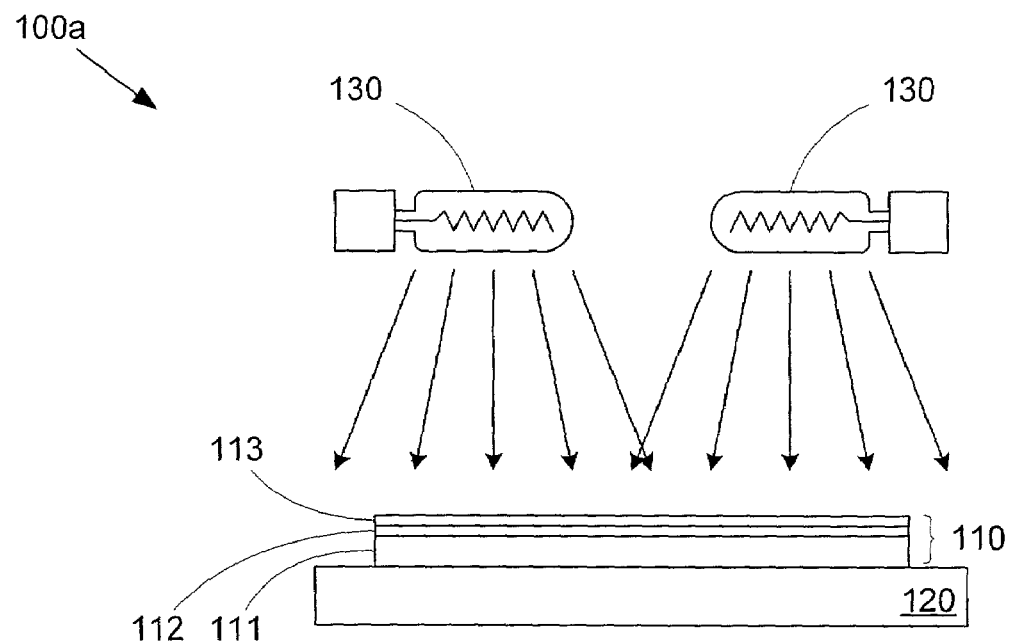
FIGS. 1a and 1b show conventional wafer cleaning systems.
Figure 1B:
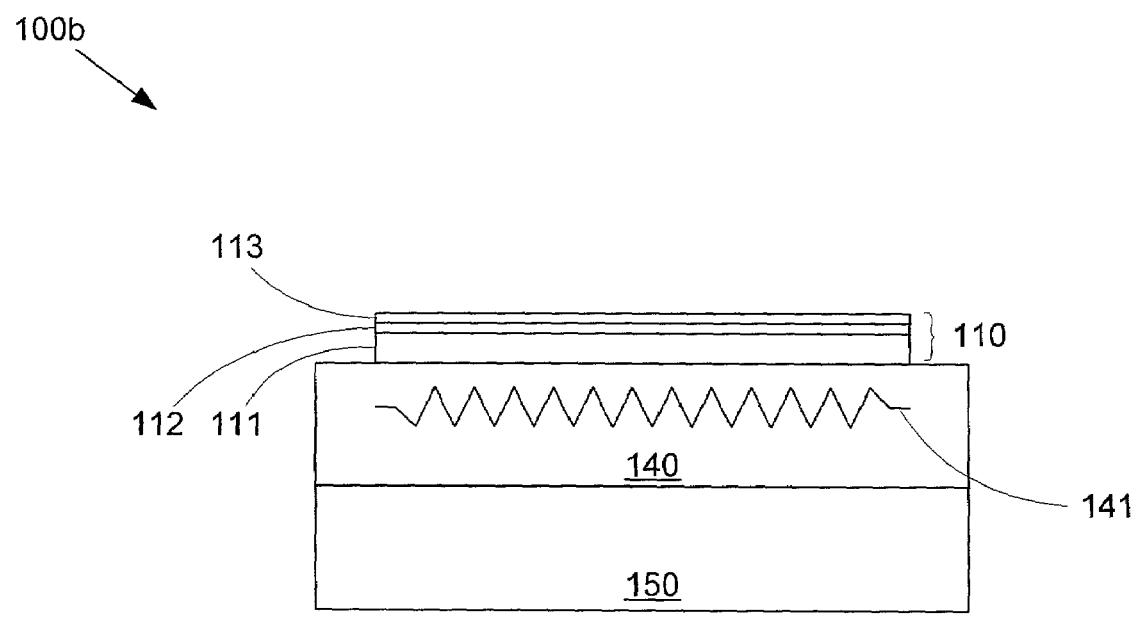
Figure 2A:
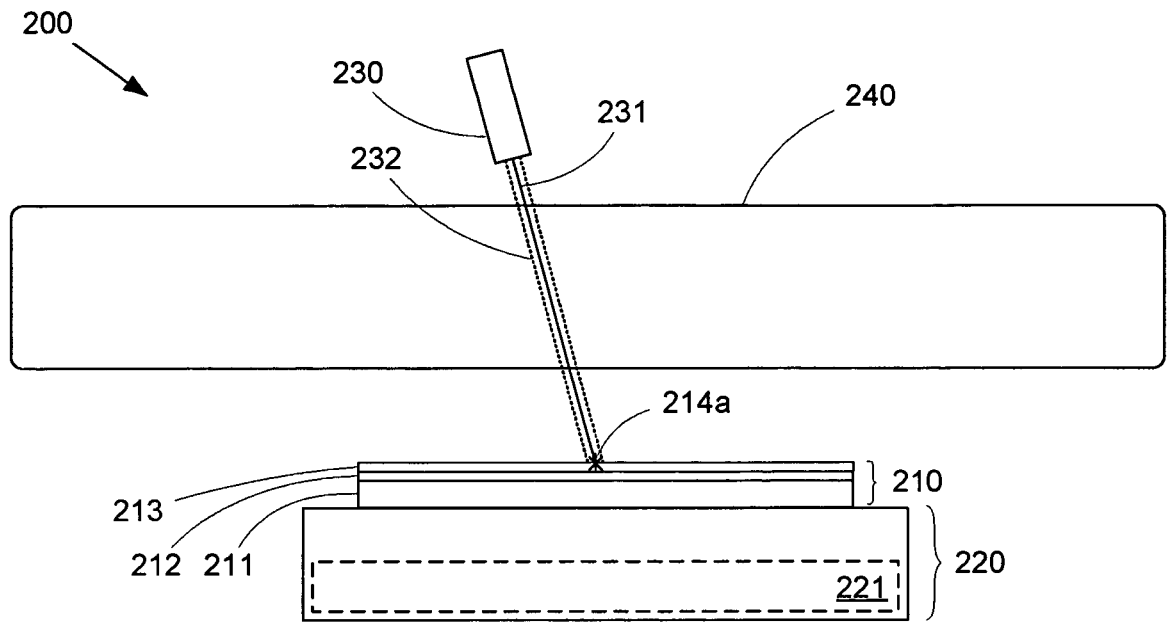
FIGS. 2a and 2b show a thin film analysis system in accordance with an embodiment of the present invention.

FIG. 2a shows a thin film analysis system 200 in accordance with an embodiment of the present invention. Analysis system 200 comprises a stage 220, an energy beam source 230, and an analysis module 240. Stage 220 holds a test sample 210 that comprises a thin film layer 212 formed on a substrate 211. Substrate 211 can comprise any structure on which thin film layer 212 can be formed, including a single-layer structure (such as a silicon wafer) or a multi-layer structure (such as an additional thin film layer or layers formed on a silicon wafer). Test sample 210 also includes a contaminant layer 213 formed on the surface of thin film layer 212. Contaminant layer 213 can comprise any unwanted material on the surface of thin film layer 212.

An analysis operation performed using analysis system 200 actually comprises two steps—a cleaning operation and a measurement operation. During the cleaning operation, a small portion of contaminant layer 213 is removed. The exposed portion (i.e., analysis area) of thin film layer 212 is then analyzed during the measurement operation. According to an embodiment of the present invention, the position of stage 220 can be shifted relative to energy beam source 230 and analysis module 240 to enable thin film analysis at multiple locations on test sample 210. According to an embodiment of the present invention, stage 220 can include a positioning mechanism 221 to enable this positional shifting.

To perform a cleaning operation, energy beam source 230 directs an energy beam 231 at a spot 214a on contaminant layer 213. Energy beam 231 is configured to remove a portion of contaminant layer 213 by heating contaminant layer 213 directly or by heating the underlying portion of thin film layer 212 or substrate 211. The portion of contaminant layer 213 heated in this manner is eventually vaporized, thereby exposing the underlying portion of thin film layer 212. As noted previously, this removal process can be aided by other mechanisms besides heating, including the direct stimulation of the bonds between contaminant layer 213 and thin film layer 212 by photons from energy beam 231.

Because the heating from energy beam source 230 is confined to a localized area, the cleaning operation can be performed very rapidly, which minimizes any impact on analysis throughput. The potential for damage to the underlying thin film layer 212 and/or substrate 211 is minimal because only a small portion of test sample 210 is heated. This risk of damage can be further reduced by performing the cleaning operation on non-functional regions of test sample 210 (e.g., regions such as scribe lines that will not be part of the functional portion(s) of the final devices to be made from test sample 210).

The amount of contaminant layer 213 to be removed depends on the measurement requirements of analysis module 240. Modern thin film analysis tools generally require an analysis area of at least 20 μm×20 μm. Therefore, at least a 20 μm×20 μm portion of contaminant layer 213 would need to be removed for such systems. However, to ensure that the entire analysis area is uniformly cleaned, a larger portion of contaminant layer 213 could be removed.

According to an embodiment of the present invention, energy beam source 230 could comprise a pulsed laser. For example, contaminant layer 213 could comprise a 5 angstrom thick layer of water and organic materials (which is similar to contamination layers often formed on modern thin film layers during production). A number of pulses or even a single pulse from a 5-100 μJoule laser having a 1-100 ns pulse duration could then heat the desired portion of contaminant layer 213 to between roughly 300° C. to 1000° C., which is a temperature range sufficient to vaporize that portion of contaminant layer 213. According to another embodiment of the present invention, energy beam source 230 could comprise a Q-switched laser delivering a relatively high peak power, such as a frequency-doubled or tripled YAG (yttrium aluminum garnet) laser operating at wavelengths of 532 nm or 355 nm, respectively. According to another embodiment of the present invention, other types of pulsed lasers operating at different wavelengths might be used including pulsed diode or alexandrite lasers. According to another embodiment of the present invention, a continuous laser, such as an argon-ion laser, could be externally modulated (such as with an acousto-optic or electro-optic modulator) to produce a pulse. According to another embodiment of the present invention, energy beam source 230 could include focusing optics such as an optical fiber 232 (shown using dotted lines) and a lens system to deliver a beam of the desired size and energy to spot 214a from a remote location, i.e., the optional optical fiber 232 could transmit energy beam 231 from a remote beam generator to spot 214a. According to another embodiment of the present invention, energy beam source 230 could comprise a flashlamp coupled to focusing optics to direct the high intensity light to the desired area on contaminant layer 213.

Figure 2B:
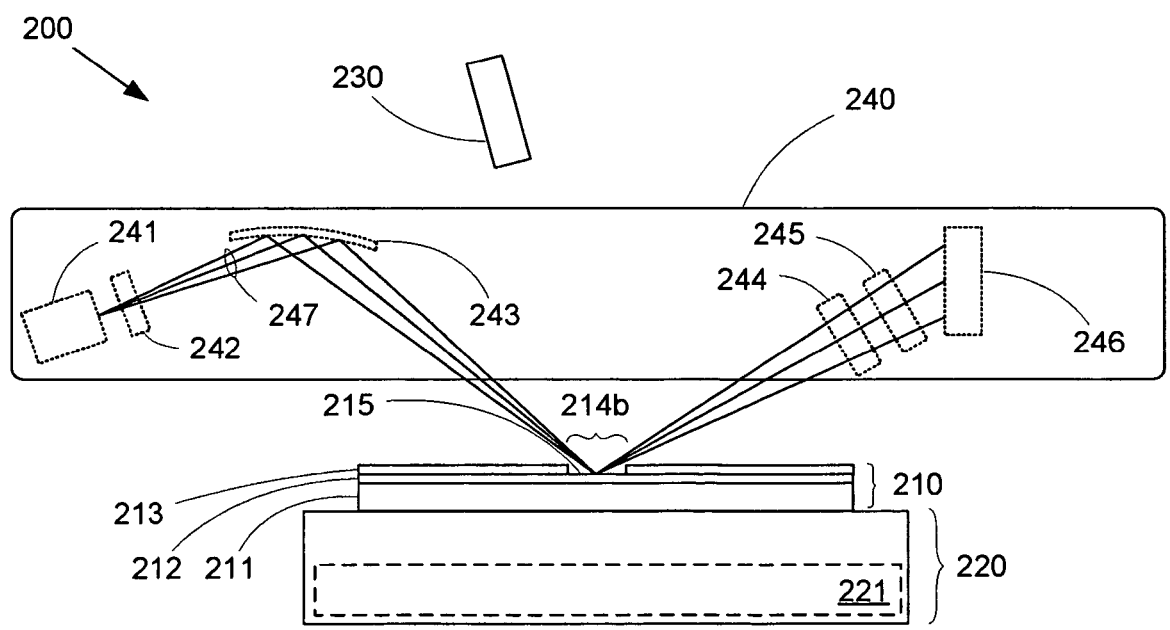

Once the cleaning operation is completed, the measurement operation can be performed. Because test sample 210 does not need to be transferred to a different tool or process chamber, the measurement operation can be performed immediately following the cleaning operation, so that the chances of recontamination of the exposed portion (analysis area) of thin film layer 212 are minimized. For explanatory purposes, FIG. 2b depicts analysis module 240 as including a xenon lamp 241, a rotating polarizer 242, a focusing mirror 243, a fixed polarizer 244, a spectrometer 245, and a CCD detector 246 for performing a spectroscopic ellipsometry analysis. However, analysis module 240 can comprise a system or systems for any type of analysis that would benefit from removal of contaminant layer 213, including SWE, SE, reflectometry (optical or x-ray), GXR, XRF, EMP, and non-contact or contact-based electrical analysis, among others. Note that analysis system 200 can comprise a conventional thin film analysis system to which energy beam source 230 is added, thereby minimizing the footprint of analysis system 200.

As indicated in FIG. 2b, contaminant layer 213 includes an opening 214b formed by the laser heating of spot 214a during the preceding cleaning operation (as shown in FIG. 2a). The measurement operation therefore can be performed directly on thin film layer 212 through opening 214b. Xenon lamp 241 directs a diverging light beam 247 through rotating polarizer 242 at focusing mirror 243, which reflects and focuses beam 247 through opening 214b in contaminant layer 213 onto an analysis area 215 on thin film layer 212. Light beam 247 is reflected by thin film layer 212 as a diverging beam, which passes through fixed polarizer 244 and spectrometer 245 before being measured by CCD detector 246 to determine the thickness of thin film layer 212.

In this manner, a localized cleaning operation can be efficiently combined with a measurement operation to ensure accurate and repeatable thin film analyses. Because both energy beam 231 and the probe beam from analysis module 240 (here represented by light beam 247) are simultaneously directed at substantially the same location on test sample 210, the position of test sample 210 does not have to be adjusted between cleaning and measurement operations. Therefore, the measurement operation can be performed immediately after the cleaning operation to ensure that a new contaminant layer is not reformed over analysis area 215.

Figure 3A:
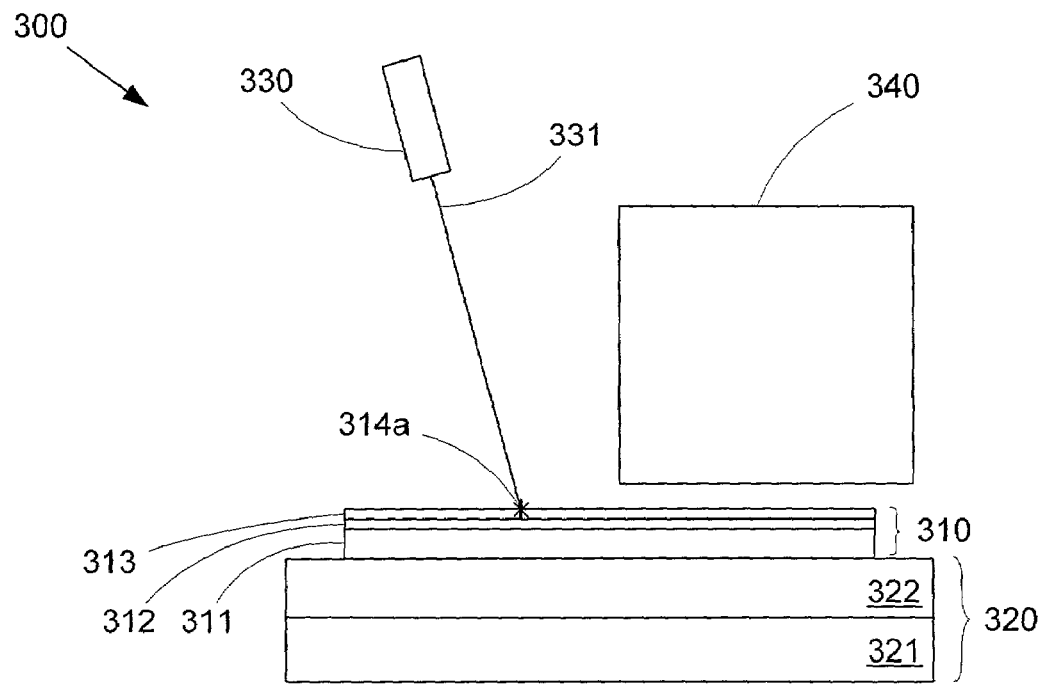
FIGS. 3a and 3b show a thin film analysis system in accordance with another embodiment of the present invention.

FIG. 3a shows a thin film analysis system 300 in accordance with an embodiment of the present invention. Analysis system 300 comprises a stage 320, an energy beam source 330, and an analysis module 340. Stage 320 includes a positioning mechanism 321 and a platform 322. Positioning mechanism 321 allows the position of platform 322 to be shifted relative to energy beam source 330 and analysis module 340. Platform 322 holds a test sample 310 that comprises a thin film layer 312 formed on a substrate 311. Substrate 311 can comprise any material on which thin film layer 312 can be formed, including a single material (such as a silicon wafer) or a plurality of materials (such as an additional thin film layer or layers formed on a silicon wafer). Test sample 310 also includes a contaminant layer 313 formed on the surface of thin film layer 312. Contaminant layer 313 can comprise any unwanted material on the surface of thin film layer 312.

Unlike in analysis system 200 shown in FIGS. 2a and 2b, energy beam source 330 and analysis module 340 are not simultaneously focused at the same location on test sample 310. Consequently, an analysis operation performed using analysis system 300 actually comprises three steps—a cleaning operation, a positioning operation, and a measurement operation. During the cleaning operation, a small portion of contaminant layer 313 is removed by the energy beam from energy beam source 330. Then during the positioning operation, test sample 310 is positioned such that the probe beam of analysis module 340 is aligned with the portion of thin film layer 312 exposed during the cleaning operation. The exposed portion of thin film layer 312 can then be analyzed by analysis module 340 during the measurement operation.

To perform a cleaning operation, energy beam source 330 directs an energy beam 331 at a point 314a on contaminant layer 313. Energy beam 331 is configured to remove a portion of contaminant layer 313 by heating contaminant layer 313 directly or by heating the underlying portion of thin film layer 312 or substrate 311. The portion of contaminant layer 313 heated in this manner is vaporized, thereby exposing the underlying portion of thin film layer 312.

Because the heating from energy beam source 330 is confined to a localized area, the cleaning operation can be performed very rapidly, which minimizes any impact on analysis throughput. The potential for damage to the underlying thin film layer 312 and/or substrate 311 is minimal because only a small portion of test sample 310 is heated. This risk of damage can be further reduced by performing the cleaning operation on nonfunctional regions of test sample 310.

The amount of contaminant layer 313 to be removed depends on the measurement requirements of analysis module 340. As described previously, modern thin film analysis tools generally take measurements within a roughly 20 µm×20 µm spot. Accordingly, energy beam source 330 could comprise a 5-100 µJoule pulsed laser with a pulse duration of 1-1000 ns, which would be capable of vaporizing a 20 µm×20 µm (or slightly larger) portion of a 5 angstrom thick contaminant layer (contaminant layer 313) of adsorbed water vapor. According to an embodiment of the present invention, energy beam source 330 could comprise a Q-switched laser delivering a relatively high peak power, such as a frequency-doubled or tripled YAG (yttrium aluminum garnet) laser operating at wavelengths of 532 nm or 355 nm, respectively. According to another embodiment of the present invention, energy beam source 330 could include focusing optics such as an optical fiber and a lens system to deliver a beam of the desired size and energy to spot 314a from a remote location, i.e., the optical fiber could transmit energy beam 331 from a remote beam generator to spot 314a. According to another embodiment of the present invention, energy beam source 330 could comprise a flashlamp coupled to focusing optics to direct the high intensity light to the desired area on contaminant layer 213.

Figure 3B:
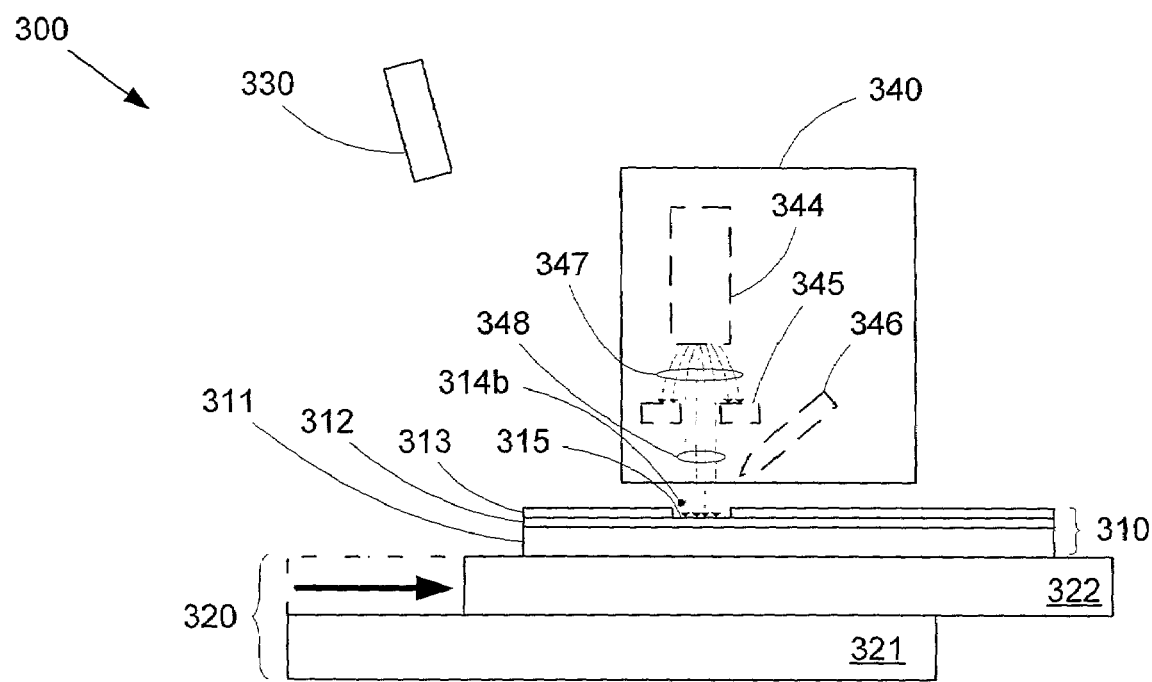

As indicated in FIG. 3b, the cleaning operation creates an opening 314b in contaminant layer 313 (at spot 314a shown in FIG. 3a), thereby exposing an analysis area 315 of thin film layer 312. A positioning operation then aligns analysis area 315 with the probe beam from analysis module 340, in this case an electron beam (e-beam) 346. This positioning operation is performed by positioning mechanism 321, which shifts platform 322 relative to analysis module 340 (as indicated by the phantom lines). While a lateral shift is indicated in FIG. 3b, any other type of positioning motion could be used, including a rotational or vertical shift. In this manner, the probe beam focusing optics in analysis module 340 can be maintained at a distance from the portion of contaminant layer 313 being removed during the cleaning operation (point 314a shown in FIG. 3a). This in turn minimizes the risk of any of vaporized contaminant layer 313 redepositing on the probe beam focusing optics or probe structure of analysis module 340.

After the positioning operation is completed, the measurement operation can be performed by analysis module 340. Because test sample 310 does not have to be transferred to a different tool or process chamber, there is little chance of recontamination of analysis area 315. For explanatory purposes, FIG. 3b depicts analysis module 340 as including a corona discharge gun 344, a charge mask 345, and a vibrating probe 346 for performing a non-contact electrical analysis, as described in co-owned U.S. Pat. No. 5,485,091. However, analysis module 340 can comprise a system or systems for any type of analysis that would benefit from removal of contaminant layer 313, including SWE, SE, reflectometry, GXR, XRF, EMP, and non-contact or contact-based electrical analysis, among others. Note that analysis system 300 can comprise a conventional thin film analysis system to which energy beam source 330 is added, thereby minimizing the footprint of analysis system 300.

As indicated in FIG. 3b, the measurement operation is performed through opening 314b formed in contaminant layer 313 during the preceding cleaning operation. Corona discharge gun 344 produces a corona discharge 347 that is shaped into a negative charge beam 348 by charge mask 345. Negative charge beam 348 deposits a negative charge onto analysis area 315 through opening 314b in contaminant layer 313. The resulting change in surface potential can then be measured by vibrating probe 346 to determine the thickness and electrical properties of thin film layer 312.

In this manner, a localized cleaning operation can be efficiently combined with a measurement operation to ensure accurate and repeatable thin film analyses. By allowing the position of test sample 310 to be shifted between the cleaning and measurement operations, energy beam 331 and the probe beam of analysis module 340 (here represented by negative charge beam 348) do not need to be focused at the same location on test sample 310. Therefore, the focusing optics of analysis module 340 can be distanced from any contamination released during the cleaning operation.

Although the present invention has been described in connection with several embodiments, it is understood that this invention is not limited to the embodiments disclosed, but is capable of various modifications that would be apparent to one of ordinary skill in the art. Thus, the invention is limited only by the following claims.

What is claimed is:

1. A thin film analysis system for analyzing a test sample, the test sample comprising a thin film formed on a substrate and a contaminant layer formed on the thin film, the thin film analysis system comprising:
    an energy beam source for directing an energy beam at the contaminant layer during a localized cleaning operation, the energy beam being configured to heat only a small area of the contaminant layer until the small area is vaporized, thereby creating an opening in the contaminant layer; and
    a thin film analysis module for performing at least one of single wavelength ellipsometry (SWE), spectroscopic ellipsometry (SE), reflectometry, grazing incidence x-ray reflectometry (GXR), x-ray fluorescence (XRF), electron microprobe analysis (EMP), non-contact-based electrical analysis, and contact-based electrical analysis on the thin film through the opening in the contaminant layer.

2. The thin film analysis system of claim 1, wherein the energy beam source comprises a continuous laser modulated to produce a pulse.

3. The thin film analysis system of claim 1, wherein the energy beam source comprises a laser having a pulse energy between approximately 5 to 100 µJoules.

4. The thin film analysis system of claim 1, wherein the energy beam source comprises an optical fiber for transmitting the laser beam from an energy beam generator to the portion of the contaminant layer.

5. The thin film analysis system of claim 1, wherein the energy beam source comprises a flashlamp.

6. The thin film analysis system of claim 1, wherein the opening in the contaminant layer exposes a non-functional region of the test sample.

7. The thin film analysis system of claim 1, wherein the opening in the contaminant layer comprises a length and a width, wherein the length and the width are both approximately 20 µm.

8. The thin film analysis system of claim 1, wherein the thin film analysis module is configured to direct a probe beam at the test sample through the opening in the contaminant layer during the measurement operation, wherein the probe beam is focused on a first location on the test sample and the energy beam is focused on a second location on the test sample, the first location and the second location being substantially the same.

9. The thin film analysis system of claim 1, wherein the thin film analysis module is configured to apply a probe structure to the thin film through the opening in the contaminant layer during the measurement operation, wherein the probe structure is aimed at a first location on the test sample and the energy beam is focused on a second location on the test sample, the first location and the second location being substantially the same.

10. The thin film analysis system of claim 1, wherein the energy beam source comprises a pulsed laser.

11. The thin film analysis system of claim 10, wherein the pulsed laser comprises a pulsed diode laser.

12. The thin film analysis system of claim 10, wherein the pulsed laser comprises an alexandrite laser.

13. The thin film analysis system of claim 10, wherein the pulsed laser comprises a Q-switched laser.

14. The thin film analysis system of claim 13, wherein the Q-switched laser comprises a yttrium aluminum garnet (YAG) laser.

15. The thin film analysis system of claim 14, wherein the YAG laser operates at a wavelength of approximately 532 nm.

16. The thin film analysis system of claim 14, wherein the YAG laser operates at a wavelength of approximately 355 nm.

17. A method for analyzing a test sample, wherein a contaminant layer covers a thin film of the test sample, the method comprising:
   placing the test sample on a stage;
   during a localized cleaning operation, directing an energy beam at a first location on the contaminant layer while the test sample is on the stage, the energy beam heating only a small area of the contaminant layer until the small area is vaporized, thereby removing a first portion of the contaminant layer to create an opening in the contaminant layer to expose a first analysis area of the thin film;
   performing at least one of single wavelength ellipsometry (SWE), spectroscopic ellipsometry (SE), reflectometry, grazing incidence x-ray reflectometry (GXR), x-ray fluorescence (XRF) electron microprobe analysis (EMP), non-contact-based electrical analysis, and contact-based electrical analysis on the thin film at the first analysis area through the opening in the contaminant layer while the test sample is on the stage; and
   generating an analysis output regarding the thin film.

18. The method of claim 17, wherein the first analysis area comprises a non-functional region of the test sample.

19. The method of claim 17, wherein the opening in the contaminant layer comprises a length and a width, wherein the length and the width are both approximately 20 μm.

20. The method of claim 17, wherein the localized cleaning operation further comprises:
   directing the energy beam at a second location on the contaminant layer, the energy beam heating only a second small area of the contaminant layer until the second small area is vaporized, thereby removing a second portion of the contaminant layer to create a second opening in the contaminant layer to expose a second analysis area of the thin film; and
   performing at least one of single wavelength ellipsometry (SWE), spectroscopic ellipsometry (SE), reflectometry, grazing incidence x-ray reflectometry (GXR), x-ray fluorescence (XRF) electron microprobe analysis (EMP), non-contact-based electrical analysis, and contact-based electrical analysis on the thin film at the second analysis area through the second opening in the contaminant layer.

21. The method of claim 17, wherein directing the energy beam comprises applying at least one pulse from a pulsed laser to the first location on the contaminant layer.

22. The method of claim 21, wherein the pulsed laser comprises a Q-switched yttrium aluminum garnet (YAG) laser.

23. A thin film analysis system for analyzing a test sample, the test sample comprising a thin film formed on a substrate and a contaminant layer formed on the thin film, the thin film analysis system comprising:
   means for directing an energy beam at the contaminant layer during a localized cleaning operation, the energy beam heating only a small area of the contaminant layer until the small area is vaporized, thereby removing a portion of the contaminant layer to create an opening in the contaminant layer to expose an analysis area on the thin film; and
   means for performing at least one of single wavelength ellipsometry (SWE), spectroscopic ellipsometry (SE) reflectometry, grazing incidence x-ray reflectometry (GXR), x-ray fluorescence (XRF), electron microprobe analysis (EMP), non-contact-based electrical analysis, and contact-based electrical analysis on the thin film at the analysis area through the opening in the contaminant layer.

24. The thin film analysis system of claim 23, wherein the means for directing the energy beam comprises a Q-switched yttrium aluminum garnet (YAG) laser.

25. The thin film analysis system of claim 23, wherein the means for performing a measurement operation comprises means for directing a probe beam at the analysis area during the measurement operation, wherein the probe beam is focused on a first location on the test sample and the energy beam is focused on a second location on the test sample, the first location and the second location being substantially the same.

26. The thin film analysis system of claim 23, wherein the means for performing a measurement operation comprises means for applying a probe structure to the analysis area during the measurement operation, wherein the probe structure is aimed at a first location on the test sample and the energy beam is focused on a second location on the test sample, the first location and the second location being substantially the same.

27. A thin film analysis system for analyzing a test sample, the test sample comprising a thin film formed on a substrate and a contaminant layer formed on the thin film, the thin film analysis system comprising:
   an energy beam source for directing an energy beam at the contaminant layer during a localized cleaning operation, the energy beam being configured to heat only a small area of the contaminant layer until the small area is vaporized, thereby remove a portion of the contaminant layer to expose an analysis area on the thin film; and
   a thin film analysis module for measuring the thin film at the analysis area, wherein the thin film analysis module comprises a contact-based electrical analysis system.

28. A method for analyzing a test sample, wherein a contaminant layer covers a thin film of the test sample, the method comprising:
   placing the test sample on a stage;
   during a localized cleaning operation, directing an energy beam at a first location on the contaminant layer while the test sample is on the stage, the energy beam heating only a small area of the contaminant layer until the small area is vaporized, thereby removing a first portion of the contaminant layer to expose a first analysis area of the thin film;

measuring the thin film at the first analysis area while the test sample is on the stage, wherein measuring the thin film comprises performing a contact-based electrical analysis; and generating an analysis output regarding the thin film.

* * * * *